United States Patent
Mohindra

(10) Patent No.: US 7,416,516 B2
(45) Date of Patent: *Aug. 26, 2008

(54) REDUCING FACIAL AGING AND APPLIANCE THEREFOR

(76) Inventor: Naresh K. Mohindra, 18 Wimpole Street, London, GB (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/562,459

(22) Filed: Nov. 22, 2006

(65) Prior Publication Data

US 2007/0117681 A1    May 24, 2007

Related U.S. Application Data

(63) Continuation-in-part of application No. 10/517,578, filed as application No. PCT/GB03/02566 on Jun. 13, 2003, now Pat. No. 7,156,774.

(30) Foreign Application Priority Data

Jun. 13, 2002 (GB) .................... 0213584.6
Jun. 13, 2002 (GB) ............... PCT/GB0302566

(51) Int. Cl.
  *A63B 23/03* (2006.01)
  *A61C 5/14* (2006.01)
(52) U.S. Cl. ............................. 482/11; 128/859
(58) Field of Classification Search ........... 482/10–11, 482/859; 128/860–861; 433/70–71, 80, 433/6, 34
See application file for complete search history.

(56) References Cited

U.S. PATENT DOCUMENTS

| | | | | |
|---|---|---|---|---|
| 4,776,792 A | * | 10/1988 | Wagner et al. | 433/71 |
| 5,104,315 A | * | 4/1992 | McKinley | 433/80 |
| 5,232,878 A | | 8/1993 | Kasuga et al. | |
| 5,266,031 A | * | 11/1993 | Marigza | 433/71 |
| 5,299,936 A | * | 4/1994 | Ueno | 433/71 |
| 5,879,155 A | | 3/1999 | Kittelson | |
| 5,899,691 A | | 5/1999 | Parker et al. | |
| 6,092,523 A | | 7/2000 | Belfer | |

(Continued)

FOREIGN PATENT DOCUMENTS

WO    WO 0035369    6/2000

*Primary Examiner*—Fenn C Mathew
(74) *Attorney, Agent, or Firm*—Michael B. Fein; Cozen O'Connor

(57) ABSTRACT

A method of reducing facial aging in a person, having an upper and lower jaw bearing anterior or posterior teeth, comprises:
  a) providing a mass produced universal dental appliance, which appliance comprises at least one part, the or each part intended in use to be in continuous contact with the teeth on either the upper or lower jaw, the or each part comprising an elongate structure at least a portion of which is formed of a durable, resilient, elastomeric material having a softening point in the range from 35 to 100° C. and has a surface which in use is in continuous contact with the occlusal biting surfaces of at least two teeth on either the upper or lower jaw, and wherein said appliance has dimensions such that in use it provides a predetermined vertical separation of the jaws which is at least 3 mm beyond the normal resting position of the jaws;
  b) fitting said mass produced universal dental appliance to at least two teeth on either the upper or lower jaw of the individual; and
  c) exercising the lower jaw passively to allow the jaw to come to rest in a new resting position, is disclosed.

An appliance for use in the method is also disclosed.

4 Claims, 2 Drawing Sheets

U.S. PATENT DOCUMENTS 6,371,758 B1 4/2002 Kittelson
6,415,794 B1 7/2002 Kittelson
6,539,943 B1 4/2003 Kittelson
6,637,436 B2 10/2003 Farrell

* cited by examiner

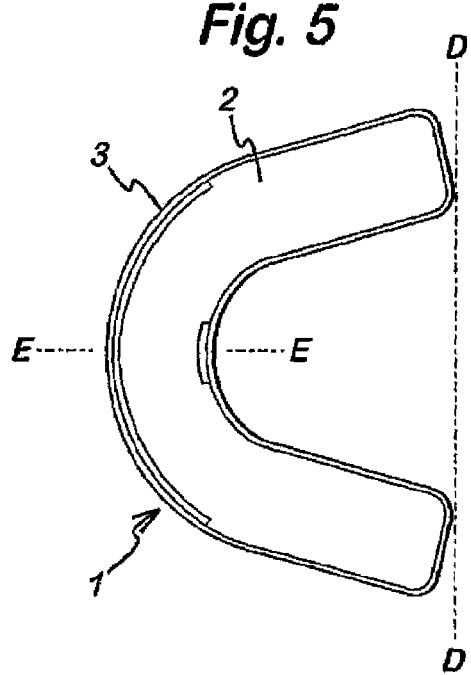
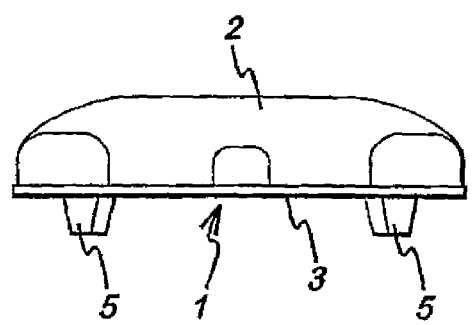
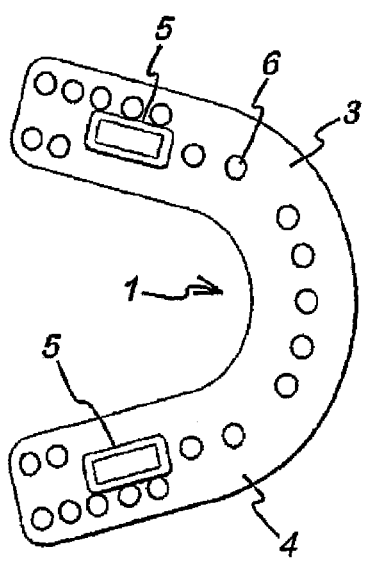
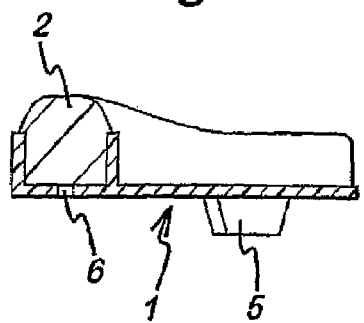

REDUCING FACIAL AGING AND APPLIANCE THEREFOR

THIS APPLICATION IS A CONTINUATION-IN-PART OF Ser. No. 10/517,578 FILED Dec. 9, 2004, NOW U.S. Pat. No. 7,156,774, WHICH WAS THE NATIONAL STAGE OF PCT/GB01/02566, FILED Jun. 13, 2003, WHICH CLAIMED PRIORITY FROM GB0213584.6 FILED Jun. 13, 2002.

BACKGROUND

This invention is concerned with a method of reducing facial aging and an appliance which is intended to be worn in the mouth during an exercise programme which, over time, can lead to a reduction in facial aging.

Pivot appliances have been used in dentistry since the 1930s to alleviate pain experienced by patients suffering from misaligned jaws, caused by inclines of the teeth. The original purpose of the pivot appliance was to separate the jaws so that inclines of the teeth would not dictate how the jaws met and thereby allow the bite of the patient to be adjusted to a more comfortable position. Use of the appliance on a temporary basis would allow the facial muscles to relax, resulting in the jaw and the condyle in the temporo mandibular joint (tmj) resting in an unrestrained position. This consequently would result in relief of pain associated with the tmj disorder.

The pivot appliance was made from a plaster mould of the patient's mouth, which mould was made by taking an impression of the lower teeth with a dental impression material. From this impression, a mould was made in plaster, which was an exact duplicate of the patient's lower jaw. This mould was then used to make a pivot appliance from a rigid moulding material, which would include wire clips to fit the appliance in the patient's mouth. The optimal thickness of the moulding material of the appliance that provided the biting surface was determined e.g. by using the command swallowing technique to establish the correct biting position for the particular patient. The patient would wear the fitted appliance under the direction and supervision of a dentist for such time until relief of pain was achieved. The appliance was then removed. The problem with this temporary procedure was that it sometimes tended to provide only temporary relief: after the appliance had been removed, there was a tendency for the jaws to return over time back to their original, painful biting position.

Some dentists would advocate that the bite of the patient had to be permanently altered to achieve permanent relief from tmj disorder. In such circumstances, orthodontic treatment was usually employed, to change the position of the teeth or by crowning the teeth.

In 1996, Dr N. K. Mohindra published a paper, in the British Dental Journal, entitled "A preliminary report on determining the vertical height of occlusion by the position of the mandible in the swallowing technique". In this paper, Dr Mohindra reported that a pivotal appliance could be used to determine the increase of the vertical dimension and resulted in dramatic increases in the vertical dimension of occlusion, e.g. by up to 19 mm, beyond the normal resting position of the mandible without patients experiencing problems. Prior to this report, doctors and dentists had considered that the vertical dimension should not be increased by more than about 2-3 mm and definitely not beyond the resting position of the jaw. The appliance used in these experiments was made in a laboratory by a trained and approved dental technician.

In 2002, Dr Mohindra published a second paper in the British Dental Journal, entitled "The effect of increasing vertical dimension on facial aesthetics". In this paper, Dr Mohindra reported that 80% of patients whose vertical dimension had been increased permanently by the use of a pivot appliance thought they looked between 5 and 20 years younger, and that these views were backed up by an independent panel who studied before and after photographs of the patients and reached same conclusions.

Subsequently, Dr Mohindra developed a facial rejuvenator which improved facial aesthetics without permanently increasing vertical dimension of occlusion. The rejuvenator, like the earlier dental appliance, required to be custom made for each patient in a laboratory by a trained dental technician. The rejuvenator comprised a substantially U-shaped layer formed from a durable, non-deformable material having a softening point over 100° C. which was custom moulded to fit over all the teeth on the lower jaw and which in use provided a bite plate. Two projections extended from the surface of the bite plate and were positioned on the bite plate over at least a part of the first molar tooth on both sides of the jaw. The projections were made of a durable, non-deformable material having a softening point over 100° C., and were custom moulded to the vertical height of occlusion for each patient, as determined by the command swallowing technique.

The rejuvenator was removable and so only increases the vertical dimension of occlusion for the short period of time when the appliance is in the mouth of the patient. The rejuvenator was based on the original pivot appliance and is made in the same way, i.e. in a laboratory by a trained and approved dental technician.

U.S. Pat. No. 6,415,794 and U.S. Pat. No. 6,539,943 disclose a dental appliance for use by athletes during periods of exertion. The appliance consists of an occlusal posterior pad made of quadruple composite material comprising four layers of distinct materials, further comprising a first layer of a durable, resilient material, a second layer of non-softenable, flexible material, a third layer of a hard, very durable material, and a fourth layer of softenable material, engageable with the occlusal surfaces to space apart the upper and lower teeth, to absorb shock and clenching stress. An adjustable arch adapted to expand and contract to be moulded to the palate is provided connecting the posterior pads together with the mouth and out of the way of the tongue to maintain the position of the occlusal posterior pads within the mouth during use and to prevent loss of the pads such as by swallowing. The appliance may be fitted using a boil and bite technique, for example by a doctor or dentist, with no requirement for customized laboratory moulding processes.

U.S. Pat. No. 6,092,523 discloses an anti-snoring device having a dental overlay portion and a guide ramp portion slidably mounted in the dental portion. The device may be fitted using a boil and bite technique, for example by a doctor or dentist, with no requirement for customized laboratory moulding processes.

SUMMARY

The object of the present invention is to provide a method of reducing facial aging using a mass produced dental appliance. A further object of the present invention is to provide an appliance for reducing facial aging that can be mass produced on an industrial basis, thereby obviating the hitherto necessity for customized manufacture in a laboratory of an appliance that has been individually designed and made for a particular patient.

In accordance with one aspect of the present invention there is provided a method of reducing facial aging in a person, the person having an upper and a lower jaw each bearing at least anterior or posterior teeth having occlusal biting surfaces, which method comprises:

a) providing a mass produced universal dental appliance, which appliance comprises at least one part, the or each part intended in use to be in continuous contact with the teeth on either the upper or lower jaw, the or each part comprising an elongate structure at least a portion of which is formed of a durable, resilient, elastomeric material having a softening point in the range from 35 to 100° C. and has a surface which in use is in continuous contact with the occlusal biting surfaces of at least two teeth on either the upper or lower jaw, and wherein said appliance has dimensions such that in use it provides a predetermined vertical separation of the jaws which is at least 3 mm beyond the normal resting position of the jaws;

b) fitting said mass produced universal dental appliance to at least two teeth on either the upper or lower jaw of the individual; and c) exercising the lower jaw passively to allow the jaw to come to rest in a new resting position. Preferably, the appliance is adapted to provide in use a predetermined vertical separation of at least 3 mm up to about 24 mm, preferably at least 5 mm e.g. from about 5 mm up to about 15 mm, and most preferably from about 8 mm e.g. about 8 mm to about 11 mm e.g. 10 mm.

In another aspect, the present invention provides a mass produced universal dental appliance suitable for use in the above method of reducing facial aging of a person. The appliance comprises at least one part, the or each part intended in use to be in continuous contact with the teeth on either the upper or lower jaw, the or each part comprising an elongate layered-composite structure comprising:

i) a first layer, formed of a durable, resilient, elastomeric material having a softening point in the range from 35 to 100° C., having a surface which in use is in continuous contact with the occlusal biting surfaces of at least two teeth on either the upper or lower jaw; and ii) a second, non-deformable layer, formed of a durable material having a softening point over 100° C., having a surface which in use provides a bite plate;

wherein the second layer of each part is provided with a non-deformable protrusion, formed of durable material having a softening point over 100° C., which protrudes at least 2 mm up to 20 mm from the surface of the bite plate away from the first layer, and wherein the appliance has dimensions such that in use it provides a predetermined vertical separation of the jaws which is at least 3 mm beyond the normal resting position of the jaws.

In one embodiment, the mass produced universal dental appliance is adapted such that in use the first layer is in continuous contact with at least two anterior teeth on either the upper or lower jaw.

In a preferred embodiment of the present invention, there is provided a mass produced universal dental appliance suitable for use in a method of reducing facial aging, which appliance comprises two parts, the parts intended in use to contact the posterior teeth on respective opposite sides of either the upper or lower jaw, each part comprising an elongate layered-composite structure comprising:

i) a first layer formed of a durable, resilient, elastomeric material having a softening point in the range from 35 to 100° C. and which in use contacts and grips the occlusal biting surfaces of the posterior teeth; and ii) a second non-deformable layer formed of a durable material having a softening point over 100° C. and which in use provides a bite plate;

wherein the second layer of each part is provided with a protrusion, formed of durable, non-deformable material having a softening point over 100° C., which extends from at least 2 mm up to 20 mm from the surface of the bite plate away from the first layer and which is positioned such that in use the protrusion extends from the surface of the bite plate above at least a part of the first and/or second molar teeth which are in contact with the first layer. In this embodiment, the appliance has dimensions such that in use it provides a predetermined vertical separation of the jaws which is at least 3 mm beyond the normal resting position of the jaws.

The universal appliance is adapted to provide a predetermined vertical separation of the jaws which is at least 3 mm beyond the normal resting position of the jaws, as determined by the command swallowing technique and, advantageously, can be either fitted by e.g. a doctor or dentist without requiring use of customized laboratory processes or a dental technician, or it may be purchased over-the-counter and fitted by the individual user. Preferably, the appliance is adapted to provide in use a predetermined vertical separation of at least 3 mm up to about 24 mm, preferably at least 5 mm e.g. from about 5 mm up to about 15 mm, and most preferably from about 8 mm e.g. about 8 mm to about 11 mm e.g. 10 mm.

The universal appliance is intended to be used by a patient to reduce the signs of facial aging. The universal appliance advantageously does not have to be made individually for a patient, unlike the rejuvenator.

The appliance may be worn at any time of the day, when the patient is awake or asleep. However, at least initially, until the patient is used to wearing the appliance and exercising the lower jaw passively, the appliance is preferably worn during the day only.

Use of the universal appliance will be generally prescribed by a doctor or a dentist or, in the case of an over-the-counter purchase, as prescribed on the accompanying instructions for use.

The appliance is preferably worn for from about ½ to about 12 hours in any day. It is recommended not to wear the appliance for 24 hours of the day.

The appliance is preferably used over a continuous period of from 4 to 14 weeks, typically 6 weeks, with a preferred interval before reuse of from 3 to 6 months e.g. 4 months.

The appliance of the present invention is preferably shaped to fit over at least the biting surface of the posterior teeth of the upper or lower jaw, preferably the lower jaw. It is preferred that the appliance is substantially U-shaped, so as to fit comfortably over both the anterior and posterior teeth or over only the anterior teeth. Alternatively, the appliance may comprise two separate portions which fit over only the posterior teeth on either side of the respective jaw, with a bridging means to connect the two portions.

Each part of the two parts of the appliance of the present invention which fit over the posterior teeth on both sides of the upper or lower jaw consists of an elongate layered-composite structure comprising i) a first layer formed of a durable, resilient, elastomeric material having a softening point in the range from about 35 to 100° C. and which in use contacts and grips the occlusal biting surfaces of the posterior teeth; and ii) a second, non-deformable layer formed of a durable material having a softening point over 100° C. and which in use provides a bite plate.

The second layer is provided with a protrusion formed of durable, non-deformable material having a softening point over 100° C. which extends from at least about 2 mm up to about 20 mm, preferably from about 5 mm up to about 15 mm, most preferably from about 7 mm to about 10 mm e.g. 9 mm, from the surface of the bite plate away from the first layer and which is positioned such that in use it is on the bite plate above at least a part of the first and/or second molar teeth which are in contact with the first layer.

The protrusion is preferably formed integrally with the second layer.

Preferably, the protrusion is centrally located above at least a part of the first and/or second molar teeth. More preferably, the width of the protrusion is less than the width of the molar(s) above which the protrusion is intended to be positioned.

The shape of the protrusion is not important, provided that in use it is comfortable for the patient. When the appliance is fitted the protrusion preferably provides a point above the first and/or second molars on the lower jaw about which the lower jaw may pivot, if forced to do so.

In another aspect, the present invention provides a method of reducing facial aging, which method comprises fitting an appliance as described above on either the upper or lower jaw, preferably the lower jaw, and exercising the lower jaw passively to allow the jaw to come to rest in a new resting position.

Exercising may be undertaken when the patient is conscious or asleep. Exercising should take place passively, for example when the patient is asleep or simply performing normal daytime activities. In such passive exercise, the facial muscles enable the jaw to adopt a new resting position. Active jaw exercise, i.e. exercise involving clenching of the jaws on to the appliance e.g. eating, should preferably be avoided whilst the appliance is fitted in the mouth for at least such time until the facial muscles have substantially adjusted to enable the jaws to come to rest voluntarily in the new resting position.

Exercising is preferably achieved by wearing the appliance continuously for from about ½ to about 12 hours in any day (it is recommended not to wear the appliance for 24 hours of the day). Exercising is preferably undertaken on a daily basis over a period of from 4 to 14 weeks, typically 6 weeks. A break from exercising of from 3 to 6 months e.g. 4 months is preferably taken before commencing another period of exercising.

The first layer of the appliance is formed of a durable, resilient, elastomeric material, preferably having a softening point in the range from about 35 to 100° C., preferably about 35 to 50° C., more preferably from about 35 to 40° C. Such materials are well known in the art and are commonly used in the manufacture of boil and bite type dental products, such as those described in U.S. Pat. No. 6,092,253, U.S. Pat. No. 6,415,794 and U.S. Pat. No. 6,539,943. Examples of suitable materials are styrene block copolymers, polyolefin rubbers, acrylate based elastomers and ethylene vinyl acetate copolymers, and mixtures thereof. Commercially available materials include Elvax and Engage available from DuPont, Kraton thermoplastic rubber available from Shell, Santoprene available from Advanced Elastomer Systems and Dynaflex available from GLS. The material used to form the first layer must become mouldable when placed in water at or close to boiling temperatures.

The first layer is preferably from 5 to 15 mm thick, more preferably 8 to 12 mm thick, before fitting. After fitting, the thickness of the layer will vary from point to point along the length appliance. Preferably, after fitting, the thickness of the first layer does not go below 1 mm.

It is the employment of the first layer material in the composite structure of the appliance that enables the appliance during fitting to adjust to provide a vertical separation of the jaws determined by the command swallow technique.

The second, non-deformable layer of the appliance is formed of a durable material having a softening point over 100° C., e.g. 150° C. or more. Such materials are well known in the art and are commonly used in the manufacture of boil and bite type dental products, such as those described in U.S. Pat. No. 6,092,253, U.S. Pat. No. 6,415,794 and U.S. Pat. No. 6,539,943. Examples of suitable materials include polycarbonate resins, high density polyethylene and polypropylene and methylmethacrylate based thermoplastics. Commercially available materials include Escorene HD-6706 available from Exxon and AP6112-HS available from Huntsman. The material used to make the second layer must not become softened in boiling water.

The second layer is preferably from about 1 to about 15 mm thick, preferably from about 3 to about 9 mm thick. The thickness of the second layer is not affected by fitting or use.

The second layer is provided with a non-deformable protrusion formed of durable material having a softening point over 100° C. which extends from at least about 2 mm up to about 20 mm, preferably from about 5 mm up to about 15 mm, most preferably from about 7 mm to about 10 mm e.g. 9 mm, from the surface of the bite plate away from the first layer and which is positioned such that in use it is on the bite plate above at least a part of the first and/or second molar teeth which are in contact with the first layer.

The appliance may comprise a third layer of material located between the first and second layers. If present, such a third layer is preferably formed of a durable resilient material having a softening point above 100° C., preferably above 150° C. Such suitable materials are mentioned above.

The protrusion is preferably formed out of the same material as the second layer and is preferably formed integrally with the second layer. Together, the protrusion and second layer are preferably no more than 22 mm thick at their thickest point, more preferably no more than 15 mm thick at their thickest point.

The appliance of the present invention can be fitted to a patient employing a similar boil and bite procedure as disclosed in U.S. Pat. No. 6,415,794, U.S. Pat. No. 6,539,943 or U.S. Pat. No. 6,092,523. The fitting should include the use of the command swallow technique.

The appliance of the present invention is useful for reducing facial aging. The aging of the face basically involves two factors. These are intrinsic and extrinsic factors. The intrinsic factors basically involve atrophy i.e. the reduction in number of cells for instance by the age of 60 (typically, we only have 60% of the muscle cells that we had when we were in our 20's).

The extrinsic factors involve damage done to cells by environmental factors e.g. sun, smoke, toxins produced by bacteria and viruses. The process involved is basically a form of chronic inflammation. Chronic inflammation in its early stages is reversible. Exercising passively with the appliance of the present invention can help reverse the process in its early stages. Accordingly, all diseases, which are related to facial aging or inflammatory conditions, could be alleviated to some extent by exercising with the appliance. For example, exercising with the appliance could help to alleviate, to some extent, some of the symptoms associated with suffers of Alzheimer's, chronic sinusitis, age related deterioration in eyesight, tangelacetasis, solar damage to the skin, acne, and bacterial infections, such as ear infections. This list is not exhaustive.

BRIEF DESCRIPTION OF THE DRAWINGS

FIG. 5 is a view from above of another appliance in accordance with the present invention.

FIG. 6 is an end view of the appliance shown in FIG. 5 along the line D-D.

FIG. 7 is a view from below of the appliance shown in FIG. 5.

FIG. 8 is a cross-sectional view of the appliance shown in FIG. 5 along the line E-E.

DETAILED DESCRIPTION

Figure 1:
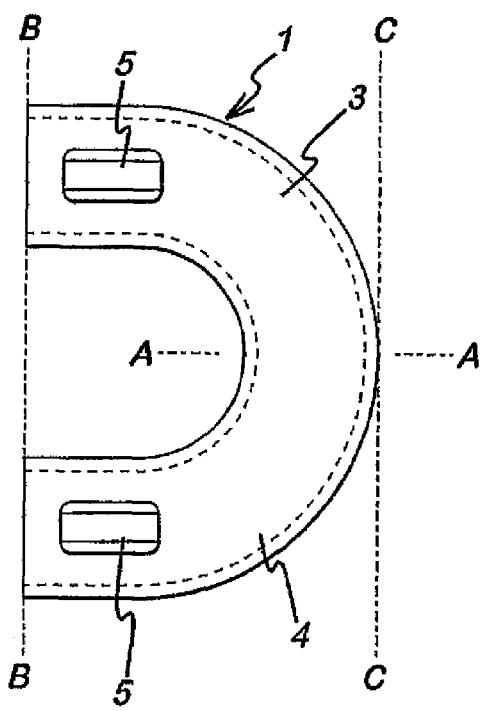
FIG. 1 is a plan view of an appliance in accordance with the present invention.
Figure 2:
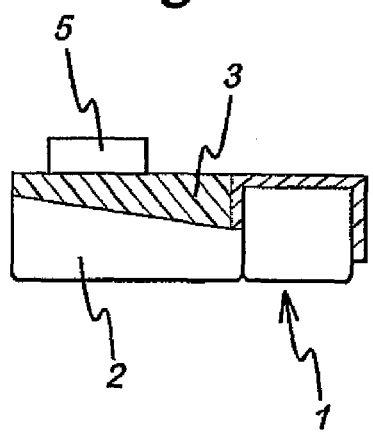
FIG. 2 is a cross-sectional view of the appliance shown in FIG. 1 along the line A-A.
Figure 3:
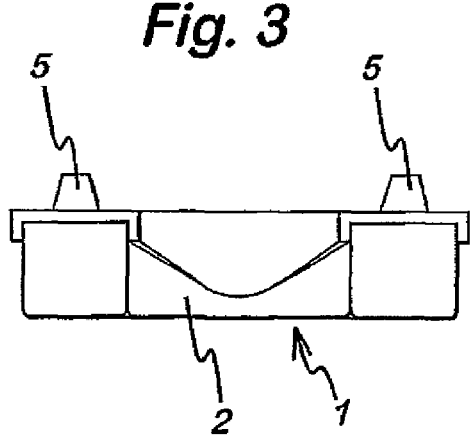
FIG. 3 is an end view of the appliance shown in FIG. 1 along the line B-B.
Figure 4:
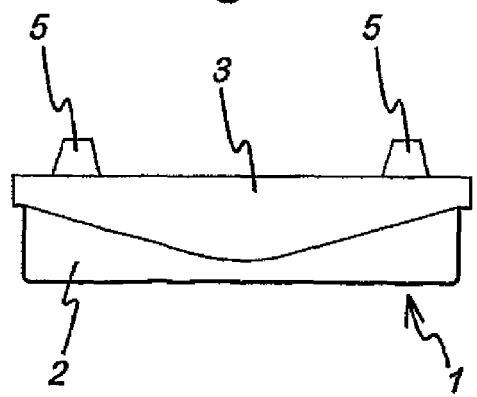
FIG. 4 is an end view of the appliance shown in FIG. 1 along the line C-C.

The invention in its various embodiments shall now be further described by way of exemplification with reference to the accompanying drawings, in which:

A U-shaped universal facial rejuvenator appliance 1, as shown in FIGS. 1-8, may comprise a first layer 2, about 10 mm thick formed of a commercially available substantially transparent elastomeric EVA copolymer having a softening point of about 360° C., and a second layer 3, about 1.5 mm thick formed of a commercially available substantially transparent polycarbonate having a softening point of about 190° C. The surface 4 of the second layer 3 remote from the first layer 2 forms, in use, a bite plate. Extending from the surface of the bite plate 4 are two projections 5 which may be formed integrally with the second layer. The projections extend approximately 3 mm above the surface 4.

The first layer 2 and second layer 3 may be adhered together, with the use of an appropriate adhesive, or may be heat formed together, If heat forming is employed, the second layer may be provided with a plurality small orifices 6 or projections into which or around which the first layer engages to secure itself in position.

The universal appliance 1 can be fitted to a patient by initially heating the appliance by submerging it in near boiling water for about 30 seconds, or such other time so as to render the material of the first layer 2 mouldable. The patient is required to open the mouth and the appliance is then placed over the teeth on the patient's lower jaw, with the first layer 2 in contact with the teeth and the two projections 5 positioned over both first molar teeth. The patient is then required to gently raise the lower jaw until the teeth on the upper jaw contact the top of the projections 5. The patient then closes their lips and swallows. The pressure applied to the to the appliance 1 by swallowing causes the material of the first layer 2 to deform and mould itself to the shape of the teeth on the lower jaw. The appliance can then be carefully removed from the mouth of the patient and submerged in cold water to accelerate the cooling of the appliance to ambient. Once the appliance has cooled, any excess of the first layer material can be trimmed away until it forms a comfortable fit.

The fitting of the appliance can readily be performed by a doctor or dentist, without the services of a dental technician or having to resort to custom moulding practices in a laboratory, or by the patient without third party assistance.

Once the appliance 1 has cooled to ambient temperatures and been trimmed, it may be used by the patient for reducing facial aging.

The process for reducing facial aging can commence as soon as the appliance has cooled to a temperature where the material used to form the first layer has solidified sufficiently for use of the appliance not to cause remoulding of that layer. The patient positions the appliance 1 in the mouth. The patient then exercises the lower jaw passively to allow the jaw to come to rest in a new resting position. The patient should, at least initially, avoid exercising the lower jaw actively about the appliance. Accordingly, wearing of the appliance e.g. during eating or sleeping should preferably be avoided whilst the appliance is fitted in the mouth for at least such time until the facial muscles have substantially adjusted to enable the jaws to come to rest voluntarily in the new resting position Once the patient is used to wearing the appliance and substantially does not involuntarily clench the jaws around the appliance, the passive exercise is preferably repeated for about 6 to 7 hours a day over a period of about 6 weeks. Before this time, however, the patient will have to get used to wearing the appliance and train themselves not to clench their jaws whilst wearing the appliance. It is therefore recommended that the patient initially uses the appliance from about only ½ hour a day and builds-up the time of use over a period of about 2-3 weeks or more thereafter, depending upon the ease with which the patient gets used to wearing the appliance and exercising passively.

The universal appliance may be tested on a sample of patients. The patients may be asked to wear the appliance at mealtimes over a specified period of time. 12 patients wore the appliance for 6 weeks, 1 for 7 weeks, 4 for 8 weeks, 2 for 9 weeks, 3 for 10 weeks, and 6 for 12 weeks. The results are as follows:

The patients were asked:

1) How comfortable was the appliance in the mouth on a scale of 0 to 3 (0 being very uncomfortable and 3 being very comfortable)?

4 patients thought it was 1 on the scale of 0 to 3, 15 thought 2, and 9 thought 3.

2) If you suffered from neckaches, headaches, shoulder pains, did these improve?

4 patients said they suffered from neck ache and 100% reported an improvement. 5 suffered from shoulder pain and 80% reported an improvement. 3 had headaches and 6% reported improvement.

3) Do you think the treatment enhanced your facial features? Give your response on a scale between 0 and 3, 0 being no improvement and 3 being good. The number of features listed was 11 and were as follows: skin above the upper eyelid, size of the eyes, crows feet, lateral droop of the eyes, bags under the eyes, improvement in skin, naso labial folds, lips, jaw line, cheeks. The results were as follows;

On an average patients noted an improvement in 7.5 of the 11 features:

skin above the upper eyelid: 60.7% noted an improvement; size of the eyes: 57.1%; crows feet: 64.3%; lateral droop of the eyes: 71% noted an improvement; bags under the eyes: 57.1%; skin: 85.7%; naso labial folds: 71.4%; lips: 89.3%; jaw line: 64.3%; neck: 64.3%; cheeks: 71.4%.

All these improvements were from mild to very good, suggesting that the universal appliance could be successfully employed to reduce facial aging.

While the invention has been described and illustrated in detail, various modifications and alternatives should become apparent to those skilled in this art without departing from the spirit and scope of the invention.

What is claimed is:

1. A mass produced universal dental appliance for use in a method of reducing facial aging of a person, the person having an upper and a lower jaw each bearing at least anterior or posterior teeth having occlusal biting surfaces, which appliance comprises at least one part, the or each part intended in use to be in continuous contact with the teeth on either the upper or lower jaw, the or each part comprising an elongate layered-composite structure comprising:
   i) a first layer, formed of a durable, resilient, elastomeric material having a softening point in the range from 35 to 100° C., having a surface which in use is in continuous contact with the occlusal biting surfaces of at least two teeth on either the upper or lower jaw; and
   ii) a second, uniform, non-deformable layer, formed of a durable material having a softening point over 100° C., having a surface which in use provides a bite plate;
   wherein the second layer of each part is provided with a non-deformable protrusion, formed of durable material having a softening point over 100° C., which protrudes at least 2 mm up to 20 mm from the surface of the bite plate away from the first layer, and wherein the appliance has dimensions such that in use it provides a predetermined vertical separation of the jaws which is at least 3 mm beyond the normal resting position of the jaws.

2. An appliance as claimed in claim 1, wherein the protrusion is formed integrally with the second layer.

3. An appliance as claimed in claim 1, wherein in use the first layer is in continuous contact with at least two anterior teeth on either the upper or lower jaw.

4. A method of reducing facial aging in a person, the person having an upper and a lower jaw each bearing at least anterior or posterior teeth having occlusal biting surfaces, which method comprises:
   a) providing a mass produced universal dental appliance, which appliance comprises at least one part, intended in use to be in continuous contact with the teeth on either the upper or lower jaw, comprising an elongate structure at least a portion of which is formed of a durable, resilient, elastomeric material having a softening point in the range from 35 to 100° C. and has a uniform surface which in use is in continuous contact with the occlusal biting surfaces of at least two teeth on either the upper or lower jaw, and wherein said appliance has dimensions such that in use it provides a predetermined vertical separation of the jaws which is at least 3mm beyond the normal resting position of the jaws;
   b) fitting said mass produced universal dental appliance to at least two teeth on either the upper or lower jaw of the individual;
   c) exercising for at least hours per day, over a period of at least 4 weeks the lower jaw passively to allow the jaw to come to rest in a new resting position; and
   d) avoiding actively exercising the lower jaw and avoiding clenching.

* * * * *

UNITED STATES PATENT AND TRADEMARK OFFICE
CERTIFICATE OF CORRECTION

| | | |
|---|---|---|
| PATENT NO. | : 7,416,516 B2 | Page 1 of 1 |
| APPLICATION NO. | : 11/562459 | |
| DATED | : August 26, 2008 | |
| INVENTOR(S) | : Naresh K. Mohindra | |

It is certified that error appears in the above-identified patent and that said Letters Patent is hereby corrected as shown below:

In the Claims

Column 10, line 26, Claim 4, "c) exercising for at least hours per day," should be read --c) exercising for at least 1/2 hours per day,--

Signed and Sealed this
Sixteenth Day of June, 2015

Michelle K. Lee
*Director of the United States Patent and Trademark Office*